| United States Patent [19] | [11] Patent Number: 5,156,966 |
|---|---|
| Takahashi et al. | [45] Date of Patent: Oct. 20, 1992 |

[54] L-CARNITINE DEHYDROGENASE AND PROCESS FOR ITS PRODUCTION

[75] Inventors: Mamoru Takahashi; Kazuo Matsuura; Shinobu Nagasawa, all of Shizuoka, Japan

[73] Assignee: Toyo Jozo Kabushiki Kaisha, Shizuoka, Japan

[21] Appl. No.: 726,200

[22] Filed: Jul. 5, 1991

Related U.S. Application Data

[62] Division of Ser. No. 596,994, Oct. 12, 1990.

[30] Foreign Application Priority Data

Oct. 13, 1989 [JP] Japan ................................ 1-267919

[51] Int. Cl.$^5$ .......................... C12N 9/04; C12N 1/00
[52] U.S. Cl. ...................................... 435/190; 435/829
[58] Field of Search .................................. 435/190, 829

[56] References Cited

U.S. PATENT DOCUMENTS

| 4,221,869 | 9/1980 | Vandecasteele et al. | 435/117 |
| 4,542,098 | 9/1985 | Vandecasteele et al. | 435/190 |

FOREIGN PATENT DOCUMENTS

| 175582 | 3/1986 | European Pat. Off. | 435/188 |
| 228974A3 | 10/1985 | German Democratic Rep. | 435/190 |
| 54-55785 | 5/1979 | Japan | 435/190 |
| 56-23891 | 3/1981 | Japan | 435/188 |
| 58-89183 | 5/1983 | Japan | 435/190 |
| 58-89200 | 5/1983 | Japan | 435/190 |
| 59-14788 | 1/1984 | Japan | 435/188 |
| 60-78581 | 5/1985 | Japan | 435/188 |
| WO85/05127 | 11/1985 | PCT Int'l Appl. | 435/188 |
| 1449581 | 1/1989 | U.S.S.R. | 435/190 |

*Primary Examiner*—David M. Naff
*Assistant Examiner*—Mike Meller
*Attorney, Agent, or Firm*—Young & Thompson

[57] ABSTRACT

An isolated L-carnitine dehydrogenase is disclosed, which is stable in solution and has a residual activity of greater than 70% after one week in a pH 9.0 buffer solution at 5° C. Also disclosed is a process for producing the new enzyme from a microorganism of the Alcaligenes genus, preferably the newly-discovered species Alcaligenes sp. No. 981 FERM BP-2570.

2 Claims, 5 Drawing Sheets

L-CARNITINE DEHYDROGENASE AND PROCESS FOR ITS PRODUCTION

This application is a division of application Ser. No. 07/596,994, filed Oct. 12, 1990.

FIELD OF THE INVENTION

The present invention relates to carnitine dehydrogenase which is stable in solution, as well as to a process for its production. More particularly, the present invention relates to carnitine dehydrogenase which is stable in solution, and which is utilizable for an assay of L-carnitine in clinical chemistry, conditioning foodstuffs and producing L-carnitine, as well as for measuring L-carnitine generated from hydrolysis of acyl-L-carnitine.

BACKGROUND OF THE INVENTION

L-carnitine is an essential substance for mediating long-chain fatty acid transport through the mitochondrian membrane prior to intracellular $\beta$-oxidation, and hence a deficiency of L-carnitine causes disorders in fatty acid and its related metabolisms. Particularly, it is believed that disorders of the skeletal muscle and cardiac muscle, both of which are high energy consumption tissues depending on carnitine and lacking in carnitine generation, occur from such deficiency. Heretofore a disease arising from inborn irregularities of carnitine metabolism has been studied, however in recent time, secondary disorders of carnitine metabolism have become a problem in patients suffering from nephrosis and undergoing dialysis. Carnitine is administered to carnitine-deficient patients who have a disease of the body muscle or cardiac muscle, or patients undergoing dialysis. Studies on the behavior of carnitine in diseases and therapy have been required, however a desirable assay method for carnitine in the clinical field has not been developed.

THE PRIOR ART

Known assay methods for carnitine are as follows:

1. L-carnitine and acetyl CoA are treated with carnitine acetyltransferase (CAT), and the thus-liberated CoASH and 5,5'-dithio-bis-2-nitrobenzoate (DTNB) are further reacted to generate thiophenolate ion which is colorimetrically measured (DTNB method). This method is described in *J. Biol. Chem.*, Vol. 238, p. 2509 (1963), *J. Lipid Res.*, Vol. 5, pp. 184-187 (1964) and *Clinical Pathology*, Vol. 36, N. 11, pp. 1296-1302 (1988).

2. L-carnitine and $^{14}$C- or $^{3}$H-labelled acetyl CoA are treated with CAT to generate labelled acetyl-L-carnitine and CoASH, and radioactivity is measured (radioisotope method). This method is described in *Clin. Chem. Acta*, Vol. 37, pp. 235-243 (1972), *J. Lipid Res.*, Vol. 17, pp. 277-281 (1976), and *J. Japan. Nut. Food. Soc.*, Vol. 41, N. 5, pp. 389-395 (1988).

3. L-carnitine and NAD+ are treated with L-carnitine dehydrogenase to generate 3-dehydrocarnitine and NADH, and increased UV absorption of NADH is measured (carnitine dehydrogenase method). This method is described in *Eur. J. Biochem.*, Vol. 6, pp. 196-201 (1968), ibid. Vol. 10, pp. 56-60 (1969), and *Fresenius Z. Anal. Chem.*, Vol. 320, N. 3, pp. 285-289 (1985).

4. L-carnitine and acetyl CoA are treated with CAT to generate CoA which is then reacted with n- {p-(2-benzimidazolyl)-phenyl}-malimide (BIPM), and the fluorescent intensity of the resulting CoA-BIPM is measured (fluorescence method). This method is described in *Ann. Rep. MHW Institute for Nerve Disease*, pp. 315-318 (1986).

Known forms of carnitine dehydrogenase itself are produced by:

*Pseudomonas aeruginosa* A 7244 (NCTC) [*Eur. J. Biochem.*, Vol. 6, pp. 196-201 (1968), ibid., Vol. 10, pp. 56-60 (1969)];

*Pseudomonas putida* IFP 206 (*Arch. Microbiol.*, Vol. 116, pp. 213-220 (1978), *Biochim. Biophys. Acta*, Vol. 957, pp. 335-339 (1988);

*Pseudomonas putida* ATCC 17633 [*Fresenius' Z. Anal. Chem.*, Vol. 320, pp. 285-289 (1985)]; and

*Xanthomonas translucens* IFO 13558 [*Agr. Biol. Chem.*, Vol. 52, pp. 851-852 (1988)].

PROBLEMS TO BE SOLVED BY THE INVENTION

In clinical chemistry, almost all biochemical reagents are provided in lyophilized form due to the stability of the reagents. Recently, long term storage of reagents in liquid has become necessary. Considering the above, reagents for assaying carnitine using L-carnitine dehydrogenase are no exception. Generally, however, enzymatic biochemical reagents are most unstable and such instability is thus an obstacle to an assay using such enzyme.

The known L-carnitine dehydrogenases are enzymes originated from bacteria such as Pseudomonas or Xanthomonas, and stability of the enzyme in solution has never been reported and is impossible to measure. Among these, L-carnitine dehydrogenase from *Pseudomonas putida* IFP 206 is reported to have an immediate loss of activity at 35° C. [*Biochem. Biophys. Acta*, Vol. 957, pp. 335-339 (1988)]; accordingly, if enzyme activity were measured at 37° C., a rapid loss of activity during assay would be expected, such that this enzyme is not used in practice.

We have sought to measure the long-term stability in solution of L-carnitine dehydrogenase from various origins, screened the L-carnitine dehydrogenase-producing bacterial strains, and consequently selected *Pseudomonas aeruginosa* NCTC A7244, *Xanthomonas translucens* IFO 13558, both of which are described in the above-identified reports, and *Pseudomonas aeruginosa* IFO 13130. These three strains were cultured according to the method described in *Eur. J. Biochem.*, Vol. 6, pp. 196-201 (1968), ibid., Vol. 10, pp. 56-60 (1969) and *Agr. Biol. Chem.*, Vol. 52, pp. 249-250 (1988). L-carnitine dehydrogenase was then isolated from the cultured mass.

The time-course stability of L-carnitine dehydrogenase at a concentration of 10 units/ml in 50 mM Tris-HCl buffer solution and pH 9.0 was measured after two weeks at 5° C. After two weeks, L-carnitine dehydrogenase obtained from the above three strains was found to have a residual activity below 50% as compared with its initial activity, especially the enzymes from *Pseudomonas aeruginosa* NCTC A7244 and IFO 13130 which had a residual activity below 30%. Therefore, the known L-carnitine dehydrogenases are considered to be unstable, such that any L-carnitine assay reagent using such enzymes would be considered unreliable due to this unstable nature.

We have therefore sought to provide L-carnitine dehydrogenase which retains more than 50% of its initial activity after two weeks in a buffer solution at 5° C.

SUMMARY AND OBJECTS OF THE INVENTION

An object of the present invention is to provide a stable L-carnitine dehydrogenase which has a property of maintaining an activity of at least 70% after treatment with Tris-HCl buffer solution at a pH of 9.0 and a temperature below approximately 5° C. for approximately one week, as compared with an activity thereof before treating.

Another object of the present invention is to provide a process for production of L-carnitine dehydrogenase which comprises culturing an L-carnitine dehydrogenase-producing microorganism belonging to the genus Alcaligenes in a nutrient medium, and isolating L-carnitine dehydrogenase therefrom.

We have found that a microorganism of the genus Alcaligenes, strain No. 981, isolated from a soil sample from a potato field in Gojo-shi, Nara prefecture, Japan, produces L-carnitine dehydrogenase having the desired stability in solution.

DETAILED DESCRIPTION OF THE INVENTION

A strain of microorganism used in the present invention belongs to the genus Alcaligenes, and the strain No. 981 isolated by the present inventors generates a preferred example of the microorganisms.

The taxonomical properties of this strain are as follows:

In an identification of a bacterial strain used in the present invention, *A Manual for Medical Bacteria* (2nd Ed.) and *Microbiological Methods* (Vol. 3) for determinative experiments, and *Bergey's Manual of Determinative Bacteriology* (8th Ed.), *Bergey's Manual of Systematic Bacteriology*, Vol. 1 (1984) and Vol. 2 (1986) are used for consultation.

A. Morphological properties:

Observations on a nutrient agar medium, cultures for 18-24 hours at 28°-30° C., are as follows:

Round edge with straight or slightly curved bacillus and single or double linked somewhat short chain. No formation of spores. Sizes are 0.4–0.6×1.2–2.5 μm. Peritrichal movement. No polymorphism.

B. Growth on various media:

Observations on various media, cultured for 18-24 hours at 28°-30° C., are as follows:

1. Nutrient agar slant medium:
    Good growth with filiform.
    Wettish with luminescence. Ocherous but no formation of soluble pigment.
2. Nutrient agar plate medium:
    Round, convex and whole round colonies. Smooth wettish surface. Ocherous or pale ocherous. No formation of soluble pigment.
3. Liquid medium (aqueous peptone):
    Good growth with uniform turbidity. Formation of pellicle at long term (over 40 hours) culture.
4. BCP milk medium:
    Alkaline after 4-5 days.

C. Physiological properties (+ = positive, (+) = weakly positive, − = negative).

| | |
|---|---|
| Gram-strain | − |
| KOH reaction | + |
| Capsule formation | − |
| Acid fastness stain | − |
| OF-test (Hugh Leifson) | No change |
| OF-test (nitrogen source: $NH_4H_2PO_4$) | 0 (oxidative) |
| Aerobic growth | + |
| Anaerobic growth | − |
| Growth temperature | |
| 41° C. | − |
| 37° C. | + |
| 15° C. | + |
| Halotolerant NaCl conc. % | |
| 0% | + |
| 5% | + |
| 7% | − |
| Growth pH | |
| pH 4.6 | − |
| pH 5.4 | + |
| pH 8.9 | + |
| pH 9.8 | − |
| Gelatin hydrolysis | − |
| Starch hydrolysis | − |
| Casein hydrolysis | − |
| Esculin hydrolysis | − |
| Cellulose hydrolysis | − |
| Tyrosine hydrolysis | − |
| Catalase production | + |
| Oxidase production | + |
| LV-reaction | − |
| Urease production (SSR) | − |
| Urease production (Chris) | − |
| Indol production | − |
| $H_2S$ production (detection: lead acetate paper) | − |
| Acetoin production ($K_2HPO_4$) | − |
| Acetoin production (NaCl) | − |
| MR test | − |
| Nitrate reduction | |
| Gas detection | + |
| $NO_2$ detection | − |
| $NO_3$ detection | − |
| Utilization on Simmons medium | |
| Citrate | + |
| Malate | + |
| Maleate | − |
| Malonate | (+) |
| Propionate | − |
| Gluconate | − |
| Succinate | + |
| Utilization on Christenssen medium | |
| Citrate | + |
| Malate | + |
| Maleate | + |
| Malonate | + |
| Propionate | − |
| Gluconate | + |
| Succinate | + |
| Gas production from glucose | − |
| Acid formation from sugar | |
| Adonitol | − |
| L(+) arabinose | (+) |
| Cellobiose | − |
| Dulsitol | − |
| Meso-erythritol | − |
| Fructose | − |
| Galactose | + |
| Glucose | + |
| Glycerin | (+) |
| Inositol | − |
| Inulin | − |
| Lactose | − |
| Maltose | − |

| | |
|---|---|
| Mannitol | − |
| Mannose | + |
| Malezitose | − |
| Melibiose | − |
| Raffinose | − |
| L(+) rhamnose | − |
| D-ribose | − |
| Salicin | − |
| L-sorbose | − |
| Sorbitol | − |
| Starch | − |
| Saccharose | − |
| Xylose | − |
| Trehalose | − |
| Poly-β-hydroxybutyrate accumulation | − |

D. Utilization of carbon sources:

Test medium: liquid medium (pH 7.0) containing carbon source 5 g, NaCl 5 g, $MgSO_4.7H_2O$ 0.2 g, $NH_4H_2PO_4$ 1.0 g and distilled water 1 l. Results are as follows:

| | |
|---|---|
| Glucose | + |
| L(+) arabinose | − |
| Fructose | + |
| Mannitol | − |
| Mannose | + |
| Gluconate | + |
| Acetate | + |
| Adipate | − |
| Pimerate | + |
| Suberate | + |
| Tartrate | + |

According to the above taxonomical properties, the microorganism displays the specific characteristics of Gram negative bacillus, namely, it is peritrichal in movement, is catalase positive and oxidase positive, does not produce acid from glucose in Hugh-Leifson medium containing peptone, and promotes oxidative decomposition of glucose and acid formation. It displays no spore formation nor polymorphism, and is aerobic.

Among Gram-negative bacillus, there are three microorganisms genera which are peritrichal in movement, namely Alcaligenes, Chromobacterium and Flavobacterium. Chromobacterium produces violet colored pigment, and Flavobacterium produces yellow colored pigment; however, the present strain does not produce pigment. Hence, the present strain belongs to the genus Alcaligenes.

Taxonomic properties of Alcaligenes in comparison with those of the present strain, according to *Bergey's Manual of Systematic Bacteriology*, Vol. 1 (1984), are illustrated by comparing *Alcaligenes faecalis* (hereinafter designated as F), *Alcaligenes denitrificans* (hereinafter designated as D) and *Alcaligenes denitrificans* subsp. *xylosoxidans* (hereinafter designated as X), as follows:

+ = positive probability over 90%.
− = negative probability over 90%.
d = not identified as + or −.

| | F | D | X | The Present Strain |
|---|---|---|---|---|
| Oxidase production | + | + | + | + |
| Nitrate reduction | − | + | + | + |
| Nitrite reduction | + | + | + | + |
| Gelatin hydrolysis | − | − | − | − |
| Acid formation in OF-medium | | | | |
| Xylose | − | − | + | − |
| Glucose | − | − | + | − |
| Acid formation in peptone-free medium | | | | |
| Xylose | | | + | − |
| Glucose | | | + | + |
| Utilization of carbon sources | | | | |
| Glucose | − | − | + | + |
| L(+) arabinose | − | − | − | − |
| Fructose | − | − | d | + |
| Mannitol | − | − | − | − |
| Mannose | − | − | d | + |
| Gluconate | − | + | + | + |
| Acetate | + | + | + | + |

According to the above comparison, the present strain No.981 has many identical properties, but has specific differences as to acid formation in OF-medium and acid formation from xylose. Accordingly, the present strain has been designated Alcaligenes sp. No. 981 and has been deposited at The Fermentation Research Institute and assigned deposit No. FERM BP-2570.

In the process of the present invention, L-carnitine dehydrogenase-producing microorganisms belonging to the genus Alcaligenes are cultured in a medium.

A preferred example of microorganism is the above-mentioned Alcaligenes sp. No. 981. Since the taxonomical properties of microorganisms are in general easily varied, microorganisms produced by natural or artificial mutation, for example mutation by ultraviolet irradiation, radiation or mutagenic chemicals such as N-methyl-N-nitro-N-nitrosoguanidine or ethylmethane sulfonate, which nonetheless belong to the genus Alcaligenes and have L-carnitine dehydrogenase-producing ability, can be used in the present invention.

Cultivation can be made by conventional bacterial culture. Since production of L-carnitine dehydrogenase can be induced by adding carnitine, it is preferably cultured in a medium containing carnitine.

Nutrient sources for the medium are, in addition to carnitine, conventional media for microorganism cultivation containing an assimilable carbon source, a digestible nitrogen source, and, if necessary, inorganic salts.

Examples of assimilable carbon sources are glucose, fructose, saccharose, sucrose and molasses, in combination or alone. Digestible nitrogen sources are for example peptone, meat extract, yeast extract and corn steep liquor, in combination or alone. In addition, metals salts such as salts magnesium, calcium, potassium, sodium, iron, manganese, etc. can be added if necessary. Other known assimilable carbon sources and nitrogen sources can also be used.

Cultivation can be made by conventional shake-culture or aeration agitation culture under aerobic conditions. On an industrial scale, submerged aeration culturing is preferable.

The culture temperature can be varied depending on the growth rate of the microorganisms and the rate of L-carnitine dehydrogenase production, and is generally 15°-37° C., preferably about 28° C. The culture time depends on the conditions and is usually 1-3 days. Cultivation should be terminated at the stage of maximum production of the enzyme.

These conditions such as composition and concentration of culture medium, culturing temperature, agitation speed and aeration rate, can be controlled according to the kind of strain and other conditions. In a liquid culture, antifoaming agents such as silicon oil and vegetable oil can be added if necessary.

L-carnitine dehydrogenase is included in microbial cells. An example of enzyme isolation involves treating a culture medium by filtration or centrifugation to separate microbial cells, followed by treating the isolated bacterial cells by ultrasonication, French press, mechanical disruption using glass beads or freezing disruption, or by enzymatic digestion with a lysozyme to obtain a crude L-carnitine dehydrogenase solution. L-carnitine dehydrogenase can be isolated from the crude enzyme solution by known mans for the isolation and purification of proteins and enzymes. For example, salting-out precipitation can be performed by adding ammonium sulfate, sodium sulfate or potassium phosphate to the crude solution containing L-carnitine dehydrogenase. Furthermore, the precipitate can be further purified, if necessary, by using a molecular sieve, chromatography, electrophoresis or ultracentrifugation.

Purification may also be performed by making use of the physico-chemical properties of L-carnitine dehydrogenase. For example, the precipitated enzyme is dissolved in water or a buffer solution, dialyzed with a semi-permeable membrane if required, and subjected to ion-exchange chromatography using DEAE-cellulose, DEAE-Sephacel, DEAE-Sepharose, DEAE-Sephadex A-50 (Pharmacia Corp.) or DEAE-Toyopearl (Toyosoda Co.), or molecular sieving means such as gel-filtration using Sephadex G-100, G-75 or Sephacryl S-200. These means can be used singly or in combination. A purified powder of L-carnitine dehydrogenase can be obtained by lyophilization with an added stabilizer, for example a sugar such as mannitol, saccharose, or sorbitol, an amino acid such as glutamic acid or glycine, or a peptide or protein such as bovine serum albumin.

The L-carnitine dehydrogenase thus obtained has the following properties:

1. Enzyme action:

The enzyme catalyzes a reaction of L-carnitine and $NAD^+$ to generate 3-dehydrocarnitine and NADH, as shown below.

L-carnitine 3-dehydrocarnitine

2. Substrate specificity:

| L-carnitine | 100% |
| --- | --- |
| Choline | 0 |
| Glycinebetaine | 0 |
| Glucose | 0 |
| Lysine | 0 |

3. Molecular weight: $51000 \pm 6000$

Measured by TSK-gel G3000 SW (Toso Co., $0.75 \times 60$ cm).

Elution: 0.1M phosphate buffer (pH 7.0) containing 0.2M NaCl.

Standard: following molecular markers (Oriental Yeast Co.) are used.

| M. W. 12,400 | Cytochrome C |
| --- | --- |
| M. W. 32,000 | adenylate kinase |
| M. W. 67,000 | enolase |
| M. W. 142,000 | lactate dehydrogenase |
| M. W. 290,000 | glutamate dehydrogenase |

4. Isoelectric point:

pH $5.3 \pm 0.6$

Measured by electrofocussing using carrier ampholyte at 4° C., 700 V, for 40 hours. The activity of a fraction of each enzyme is measured.

5. Km-value: 0.141 mM ($NAD^+$), 9.3 mM (L-carnitine)

Km-value for $NAD^+$ is measured in various concentrations of $NAD^+$ in a reaction mixture of:

100 mM Tris-HCl buffer (pH 9.0)
5 U diaphorase (Toyo Jozo Co.)
0.025% NBT (Wako Pure Chem. Co.)
1% Tween 80 (Wako Pure Chem. Co.) and
50 mM L-carnitine.

In the reaction mixture, 50 mM L-carnitine is replaced by 1 mM $NAD^+$, and the concentration of L-carnitine is varied to measure the Km-value of L-carnitine.

The results are as shown above.

6. Heat stability:

The enzyme, dissolved in 20 mM Tris-HCl buffer (pH 8.0) to produce a 1.00 U/ml solution, is incubated for one hour at various temperatures, and the residual activity is measured.

Figure 1:
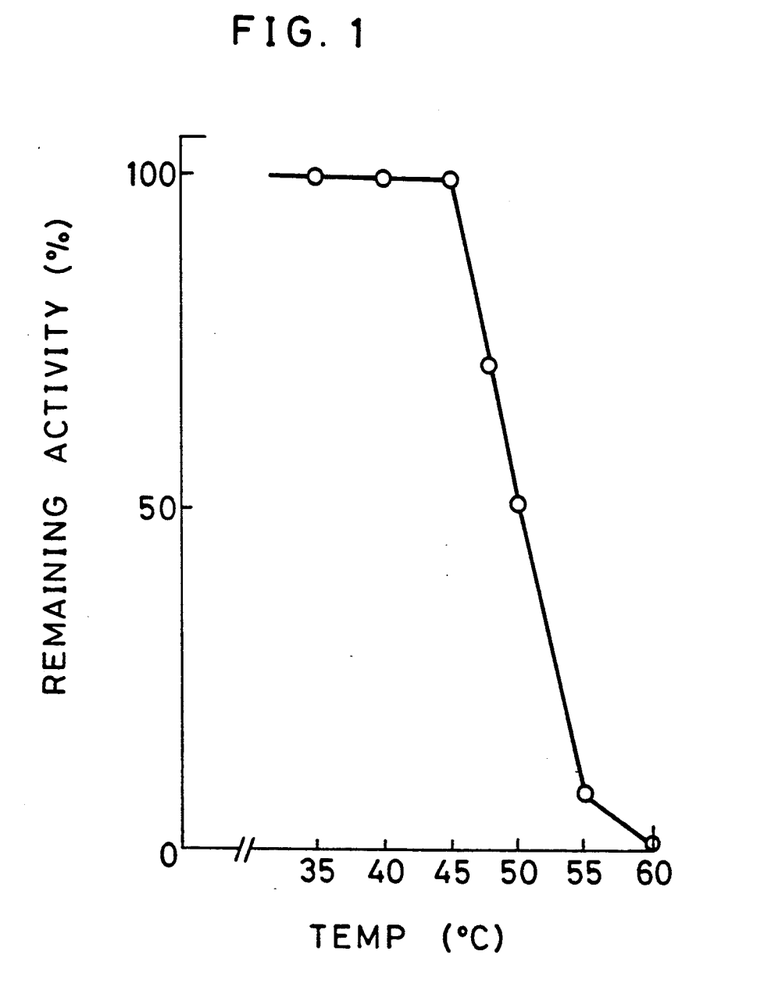
FIG. 1: heat stability of L-carnitine dehydrogenase of the present invention.

The results are shown in FIG. 1, from which it can be seen that the enzyme is stable up to 45° C.

Figure 2:
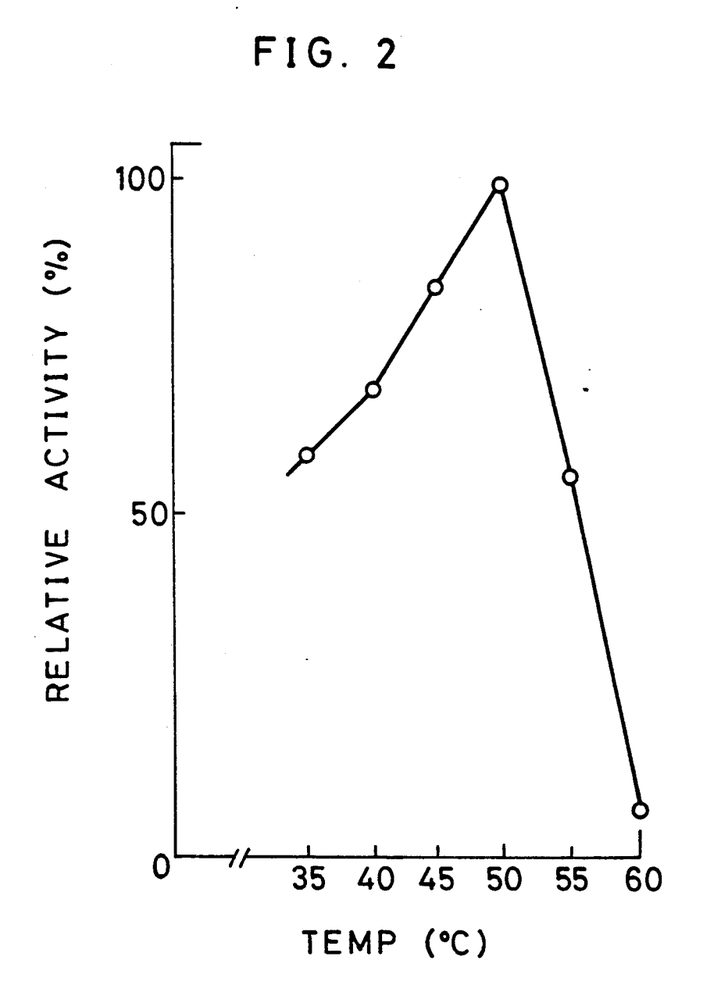
FIG. 2: optimum temperature of the enzyme of the invention.

7. Optimum temperature:

The enzyme activity is measured at 35, 40, 45, 50, 55 and 60° C., respectively, in 100 mM Tris-HCl buffer (pH 9.0) according to the assay method illustrated hereinafter. The reaction was stopped in each case after 10 mins. incubation by adding 0.1 N HCl (2 ml), whereupon the optical absorption was measured at 550 nm. As shown in FIG. 2, the enzyme shows maximum activity at 50° C.

Figure 3:
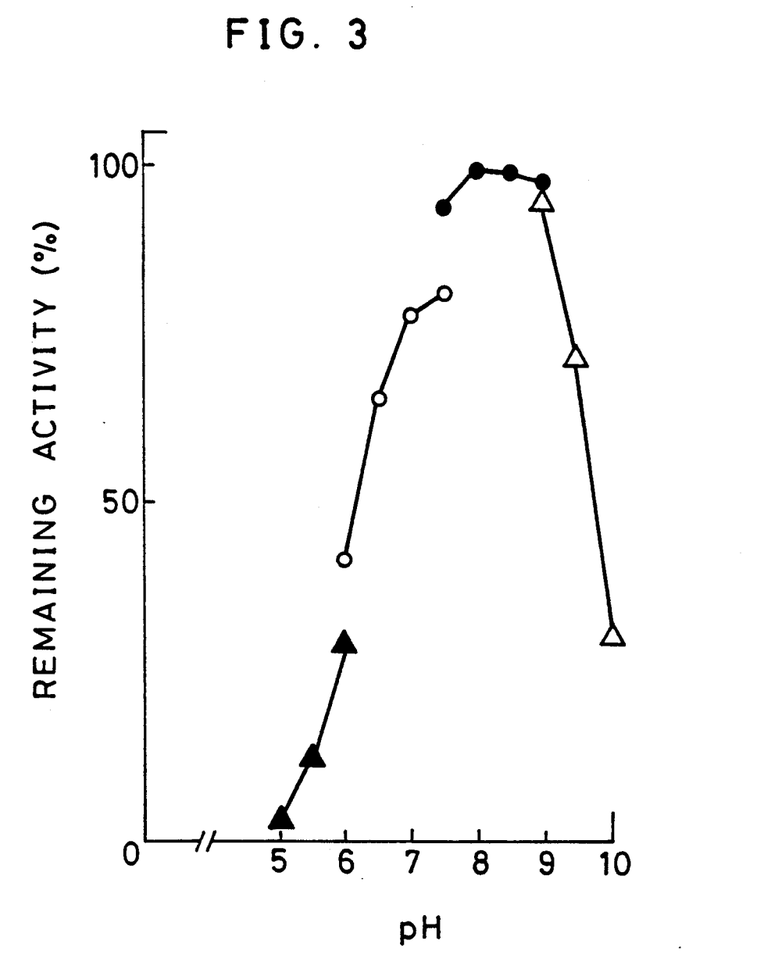
FIG. 3: pH-stability of the enzyme of the invention.

8. pH - stability:

The residual activity of the enzyme (1 U/ml, 40 mM buffer solution) is measured in various buffer solutions after heating at 45° C. for 30 mins. As shown in FIG. 3, the enzyme is stable at pH 8.0–9.0 with a residual activity of over 95%. In this figure: -▲-=acetate buffer, pH 5.6–6.0; -○-=phosphate buffer, pH 6.0–8.0; -●-=Tris-HCl buffer, pH 9.0–10.0 and -Δ-=glycine-NaOH buffer, pH 9.0–10.

9. Optimum pH: approx. pH 9.0 as shown in FIG. 4:

In an assay method for enzyme activity as illustrated hereinafter, 100 mM Tris-HCl buffer in the reaction mixture is replaced by 100 mM phosphate buffer (pH 6.5–7.0, -○-), 100 mM Tris-HCl buffer (pH 8.0–9.0, -●-) and 100 mM glycine-NaOH buffer (pH 9.0–10.0, -Δ-), and incubated at 37° C. for 10 mins. The reaction was stopped in each case by adding 0.1 N HCl, whereupon the absorption at 550 nm was measured.

Figure 4:
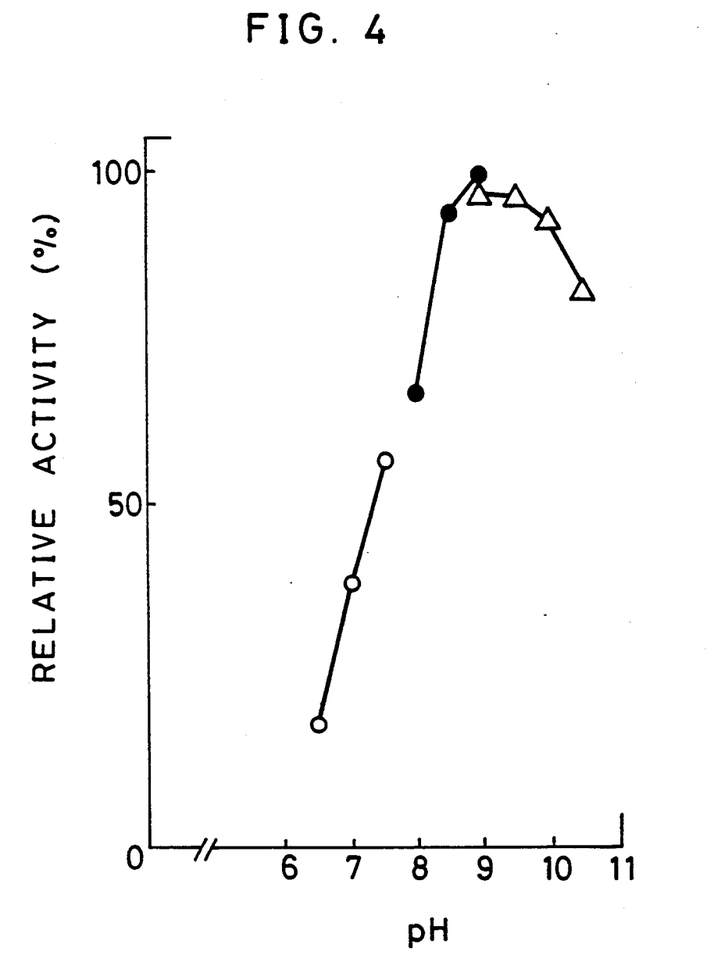
FIG. 4: optimum pH of the enzyme of the invention.

The results are shown in FIG. 4, where a maximum activity is observed at approx. pH. 9.0.

10. Long term stability in aqueous solution:

Stability of L-carnitine dehydrogenase from various origins is measured in 50 mM tris-HCl buffer (pH 9.0, 10 U/ml) at 5° C. after two weeks storage.

Figure 5:
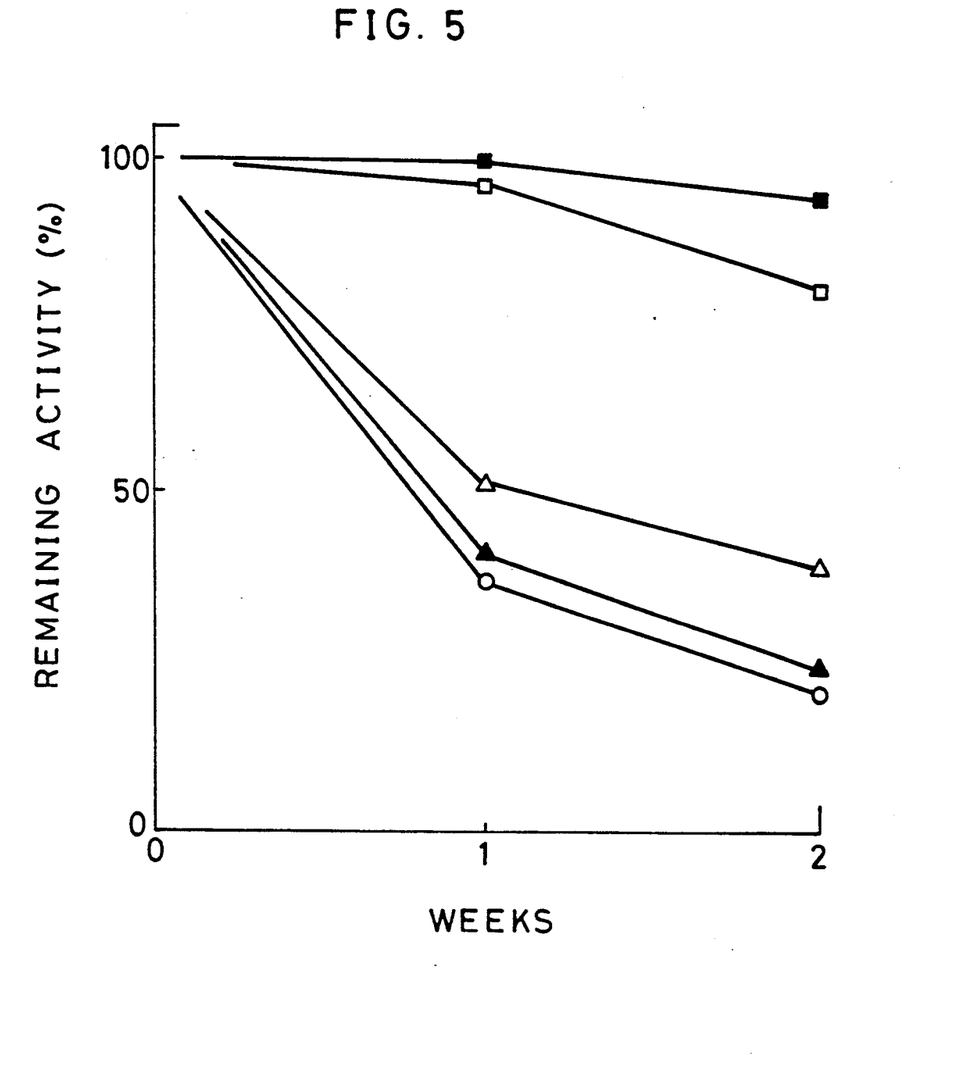
FIG. 5: stability of L-carnitine dehydrogenase obtained from known microorganisms as well as according to the present invention, in an aqueous solution.

The results are shown in FIG. 5 (-○-=L-carnitine dehydrogenase from *Pseudomonas aeruginosa* IFO 13130; -▲-=*Pseudomonas aeruginosa* NCTC A 7244; -△-=*Xanthomonas translucens* IFO 13558; -□-=Alcaligenes sp. No. 981, and -■-=L-carnitine dehydrogenase from Alcaligenes sp. No. 981 containing 0.05 mM NAD+). L-carnitine dehydrogenase obtained from aforementioned three known strains shows a residual activity of 53-40% after one week storage, and below 45% after two weeks. Especially, the enzyme from *Pseudomonas aeruginosa* IFO 13130 shows the worst residual activity of 21%.

By contrast, L-carnitine dehydrogenase of the present invention has a residual activity of 96% after one week and 82% after two weeks, thus showing superior stability as compared with enzymes from the known microorganisms. The results also show that he enzyme of the invention containing 0.05 mM NAD+ has a residual activity of 99.7% after one week and 95.1% after two weeks, demonstrating the superior stabilizing effect obtained by adding NAD+.

11. Assay method of L-carnitine dehydrogenase activity:

(1) Reaction mixture:
50 mM Tris-HCl buffer (pH 9.0)
1 mM NAD+
5 U Diaphorase (Toyo Jozo Co.)
0.05% NBT (Wako Pure Chem. Co.)
100 mM KCl
0.5% polyoxyethylene (20) sorbitan monooleate (Wako Pure Chem. Co.)
100 mM L-carnitine (Sigma Chem. Co.)

(2) Enzyme assay:

The above reaction mixture (1 ml) is incubated in a small test tube at 37° C. for 5 mins. Dilute enzyme solution (0.02 ml) is added and stirred to initiate the reaction. After exactly 10 mins., 0.1 N HCl (2.0 ml) was added and stirred to stop the reaction. Absorption at 550 nm ($A_{550}$ nm) is measured to obtain absorption $A_1$. The assay was repeated using the above reaction mixture except that L-carnitine was not included. The mixture is also treated in the same manner as described above and its absorption Ao was measured.

(3) Calculation of enzyme activity:

$$U/ml = \frac{(A_1 - A_0)}{21.7} \times \frac{1}{10} \times \frac{3.02}{0.02} \times Z$$

wherein
21.7: molecular absorption coefficient cm$^2$/μmol
Z: dilution ratio

L-carnitine dehydrogenase of the present invention, which can be produced by Alcaligenes sp. No. 981, shows a long term stability in aqueous solution such as in Tris-HCl buffer (pH 9.0) at 5° C., represented by residual activity of 96% after one week and 80% after two weeks. Accordingly, it is a stable enzyme having a stability according to which over 70% of its initial activity remains after treating for one week with Tris-HCl buffer (pH 9.0) at below 5° C. The enzyme also has superior stability upon storage in aqueous solution, as compared with enzyme from the known bacterial strains. Therefore, a stable reagent for L-carnitine assay can be prepared. Also, the enzyme of the present invention undergoes less denaturing during isolation and purification procedures, and hence it is quite easy to purify, which provides a particularly advantageous L-carnitine dehydrogenase production process.

The following examples illustrate the present invention but are not to be construed as limiting.

EXAMPLE 1

| (i) Culturing *Alcaligenes* sp. No. 981: | |
|---|---|
| DL-carnitine hydrochloride (Sigma Chem. Co.) | 3.0% |
| KH$_2$PO$_4$ | 0.2% |
| MgSO$_4$.7 H$_2$O | 0.05% |
| FeSO$_4$.7 H$_2$O | 0.002% |
| MnSO$_4$.nH$_2$O | 0.001% |
| pH 7.0 | |

100 ml of a liquid medium comprising the above composition was sterilized in a 500 ml Erlenmeyer flask at 120° C. for 20 mins. One loopful of Alcaligenes sp. No. 981 was inoculated into the medium and the medium was cultured at 28° C. with stirring at 120 rpm for 40 hours to obtain the cultured mass (95 ml) (enzyme activity: 1.2 U/ml).

| (ii) DL-carnitine hydrochloride (Sigma Chem. Co.) | 3.0% |
|---|---|
| yeast extract (Kyokuto Seiyaku Co.) | 0.1% |
| KH$_2$PO$_4$ | 0.054% |
| KH$_2$PO$_4$ | 0.746% |
| MgSO$_4$.7 H$_2$O | 0.05% |
| CaCl$_2$.2 H$_2$O | 0.002% |
| FeSO$_4$.7 H$_2$O (pH 7.0) | 0.002% |
| MnSO$_4$.nH$_2$O | 0.002% |
| disform CB 442 (Nihon Ushi Co.) | 1 ml/lit. |
| pH 7.0 | |

20 ml of a liquid medium comprising the above composition was sterilized in a 30 l jar fermenter by heating. 90 ml of the precultured seed culture obtained in step (i) above was inoculated therein and the mixture was cultured at 28° C., with aeration of 20 l/min, inner pressure 0.4 kg/cm$^2$, and agitation at 200 rpm for 27 hours to obtain the cultured mass (19 l) (enzyme activity: 3.0 U/ml).

EXAMPLE 2

Purification of enzyme:

Bacterial cells collected by centrifugation from the cultured broth (19 l) obtained in Example 1, culture (ii), were suspended in 40 mM Tris-Hcl buffer (pH 8.0) and mixed with 0.1% lysozyme and 15 ml EDTA.2 Na (5 l) and solubilized at 37° C. for one hour; then the mixture was centrifuged to remove precipitate and to obtain a supernatant solution (4500 ml) (activity: 10.3 U/ml) 1100 g ammonium sulfate was added to the supernatant solution, which was mixed well by stirring and then centrifuged to separate the precipitate. An additional 700 g ammonium sulfate was then added to the supernatant solution to dissolve the precipitate, and the solution was centrifuged to obtain a new precipitate. The new precipitate was dissolved in 40 mM Tris-HCl buffer (pH 8.0, 500 ml) (specific activity 84.1 U/ml), and the resultant solution was dialyzed against 40 mM Tris-HCl buffer (pH 8.0, 10 lit.) The dialyzed enzyme solution was charged on a column of DEAE-Sepharose CL-6B (Pharmacia Co.) (200 ml) which was buffered with 40 mM Tris-HCl buffer (pH 8.0), washed with 40 mM Tris-HCl buffer containing 0.1M KCl, (pH 8.0, 1 lit.) and eluted with 40 mM Tris-HCl buffer containing 0.3M KCl (pH 8.0) to obtain an enzyme solution (300 ml, specific activity 120.5 U/ml). The enzyme solution was dialyzed against 40 mM Tris-HCl buffer (pH 8.0, 10 lit.) The dialyzed enzyme solution was charge don a column of hydroxylapatite (KOKEN Co., 100 ml), washed with 40 mM Tris-HCl buffer (pH 8.0, 200 ml), then eluted with 2 mM phosphate buffer (pH 7.0, 100 ml) to obtain enzyme solution (100 ml, specific activity 331 U/ml). The thus-obtained enzyme solution was dialyzed against 20 mM phosphate buffer (pH 7.5, 5 lit.) to obtain 95 ml of an enzyme solution having a specific activity of 331 U/ml. The yield was 67.8%.

The purified L-carnitine dehydrogenase was found to have an NADH oxidase activity of less than 0.0001 U/ml.

Although the present invention has been described in connection with various preferred embodiments thereof, it will be appreciated that these embodiments are provided solely for purposes of illustration, and should not be construed as limiting the scope of the invention. Other embodiments and applications of the invention will be readily apparent to those skilled in the art from reading the present specification and practicing the techniques described herein, without departing whatsoever from the scope and spirit of the appended claims.

What is claimed is:

1. A process for the production of L-carnitine dehydrogenase, comprising culturing a microorganism of the genus Alcaligenes in a nutrient medium and isolating the L-carnitine dehydrogenase from the cultured mass.

2. The process according to claim 1, wherein the microorganism is Alcaligenes sp. No. 981 FERM BP-2570.

* * * * *